United States Patent
Suzuki et al.

(10) Patent No.: US 12,358,210 B2
(45) Date of Patent: Jul. 15, 2025

(54) RESIN COMPOSITION FOR STEREOLITHOGRAPHY

(71) Applicant: KURARAY NORITAKE DENTAL INC., Kurashiki (JP)

(72) Inventors: Kenji Suzuki, Niigata (JP); Shumei Ishihara, Tokyo (JP); Misaki Ito, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 334 days.

(21) Appl. No.: 17/908,937

(22) PCT Filed: Mar. 5, 2021

(86) PCT No.: PCT/JP2021/008829
§ 371 (c)(1),
(2) Date: Sep. 2, 2022

(87) PCT Pub. No.: WO2021/177462
PCT Pub. Date: Sep. 10, 2021

(65) Prior Publication Data
US 2023/0096105 A1 Mar. 30, 2023

(30) Foreign Application Priority Data
Mar. 6, 2020 (JP) .................................. 2020-038883

(51) Int. Cl.
| | |
|---|---|
| *B29C 64/124* | (2017.01) |
| *B33Y 10/00* | (2015.01) |
| *B33Y 70/00* | (2020.01) |
| *B33Y 80/00* | (2015.01) |
| *B29K 33/00* | (2006.01) |
| *B29K 105/00* | (2006.01) |
| *B29K 105/16* | (2006.01) |
| *B29L 31/00* | (2006.01) |

(52) U.S. Cl.
CPC ............ *B29C 64/124* (2017.08); *B33Y 10/00* (2014.12); *B33Y 70/00* (2014.12); *B33Y 80/00* (2014.12); *B29K 2033/26* (2013.01); *B29K 2105/0002* (2013.01); *B29K 2105/16* (2013.01); *B29L 2031/7536* (2013.01)

(58) Field of Classification Search
CPC . A61K 6/887; A61K 6/71; A61K 6/17; A61K 6/62; A61K 6/60; C08F 2/44; C08F 2/48; C08F 2/50; B33Y 70/10; B33Y 10/00; B33Y 70/00; B33Y 80/00; B29C 64/124; C08K 9/00; C08K 7/18; C08K 2201/003; C08L 33/26; C08L 33/08; C08L 33/10; B29K 2105/0002; B29K 2105/16; B29K 2033/26; A61C 13/08; A61C 13/087; B29L 2031/7536
See application file for complete search history.

(56) References Cited

U.S. PATENT DOCUMENTS

| | | | |
|---|---|---|---|
| 4,512,743 | A | 4/1985 | Santucci et al. |
| 5,849,459 | A | 12/1998 | Hagiwara et al. |
| 2013/0172441 | A1 | 7/2013 | Takahata et al. |
| 2019/0254936 | A1 | 8/2019 | Suzuki et al. |

FOREIGN PATENT DOCUMENTS

| | | |
|---|---|---|
| JP | H08-224790 A | 9/1996 |
| JP | 2000159621 A | 6/2000 |
| JP | 2006208637 A | 8/2006 |
| JP | 2006348214 A | 12/2006 |
| JP | 2013071921 A | 4/2013 |
| JP | 2015182963 A | 10/2015 |
| WO | WO-2012042911 A1 | 4/2012 |
| WO | WO-2018074380 A1 | 4/2018 |
| WO | WO-2019048963 A1 | 3/2019 |

OTHER PUBLICATIONS

Extended European Search Report issued Feb. 1, 2024 in corresponding European Patent Application No. 21764161.2, 9 pages.
International Search Report issued Apr. 20, 2021 in PCT/JP2021/008829 (with English translation), 5 pages.
Written Opinion issued Apr. 20, 2021 in PCT/JP2021/008829 (with English translation), 10 pages.

*Primary Examiner* — Monica A Huson
(74) *Attorney, Agent, or Firm* — Element IP, PLC

(57) ABSTRACT

The present invention provides a resin composition for stereolithography that is easily shapable with good shape precision while reducing sedimentation of inorganic particles during storage, and a obtained three-dimensional shaped article thereby excels in mechanical characteristics such as flexural strength and flexural modulus, in addition to having a desirable shade and good shade stability. The present invention relates to a resin composition for stereolithography comprising a polymerizable monomer (a), a photopolymerization initiator (b), an inorganic particle (c) having an average particle diameter of 5 to 500 nm, and a hindered phenolic compound (d), wherein the content of the photopolymerization initiator (b) is 0.1 to 10 parts by mass relative to 100 parts by mass of the polymerizable monomer (a), the content of the inorganic particle (c) is 50 to 400 parts by mass relative to 100 parts by mass of the polymerizable monomer (a), and the content of the hindered phenolic compound (d) is 0.1 to 500 parts by mass relative to 100 parts by mass of the photopolymerization initiator (b).

23 Claims, No Drawings

RESIN COMPOSITION FOR STEREOLITHOGRAPHY

TECHNICAL FIELD

The present invention relates to a resin composition for stereolithography. More specifically, the present invention relates to a resin composition for stereolithography that is easily shapable with good shape precision by photo-solidification (for example, bottom-up vat stereolithography) while reducing sedimentation of inorganic particles during storage, and that enables production of a three-dimensional shaped article that, in addition to having a desirable shade and good shade stability, excels in mechanical characteristics such as flexural strength and flexural modulus.

BACKGROUND ART

Photo-solidification has gained popularity as a technique to produce a three-dimensional shaped article through a repeated procedure whereby a liquid photocurable resin is cured into a thin layer under controlled application of necessary amounts of light energy, and another layer of photocurable resin is cured on the cured layer under controlled application of light after supplying another portion of the liquid photocurable resin onto the previously formed cured layer.

Vat stereolithography is a technique typically used for optical fabrication of a three-dimensional shaped article. In this technique, a computer-controlled ultraviolet laser is selectively applied to draw a desired pattern on the surface of a liquid photocurable resin composition placed in a vat. By being cured, the resin forms a layer of a predetermined thickness, and another cured layer is continuously formed on the cured layer by applying an ultraviolet laser to the liquid photocurable resin composition supplied onto the previously cured layer in the amount necessary to form a single layer. The layering process is repeated to produce a three-dimensional shaped article of the desired shape. This technique has attracted great interest because it enables easy and precision production of the desired three-dimensional shaped article in a relatively short time period, even when the product has a very complex shape. Traditionally, vat stereolithography has adopted a mode whereby an object being formed is lowered down in a vat filled with a large quantity of liquid photocurable resin composition. However, this type of vat stereolithography is being replaced by what is generally called the "bottom-up method", which is becoming mainstream because it requires less liquid photocurable resin composition and is less wasteful.

Three-dimensional shaped articles produced by stereolithography are used in an increasingly wider range of applications, from simple concept models to more complex models such as test models and prototypes. This has created a demand for higher shape precision in these three-dimensional shaped articles. In addition to satisfying such properties, these products are also required to have properties that are suited for their intended use. The field of dental materials is thought to greatly benefit from stereolithography because crowns and bridges, or prostheses as they are collectively called, require shapes that vary from patient to patient, aside from being complex in shape. However, the levels of shape precision (conformity) and mechanical characteristics required for these applications are extremely high. Inorganic particles are generally added to a resin composition for stereolithography to improve the mechanical characteristics of the cured product. A problem, however, is that adding inorganic particles to a resin composition for stereolithography increases the viscosity of the resin composition for stereolithography, and makes it difficult to shape the composition. Sedimentation of inorganic particles during storage is also an issue. It is often inevitable to use inorganic particles of small particle sizes if sedimentation of inorganic particles during storage were to be avoided, or when the size of inorganic particles is restricted by the pitch of layers as in the case of stereolithography. In either case, the viscosity of the resin composition for stereolithography increases even more greatly. The influence of viscosity becomes even more prominent particularly in bottom-up vat stereolithography because, with the small liquid volume used in this technique, the resin composition for stereolithography cannot be smoothly delivered to the surface being shaped. The material transparency tends to improve as the particle size of inorganic particles decreases. However, coloring or discoloration by a ultraviolet laser becomes more noticeable.

Against this background, Patent Literature 1 proposes containing a specific amount of benzotriazole ultraviolet absorber as a technique to impart high shape precision to a resin composition for stereolithography. A technique to achieve appropriate fluidity is also available. For example, Patent Literature 2 proposes containing a specific amount of fine inorganic particles having a specific particle diameter.

CITATION LIST

Patent Literature

Patent Literature 1: JP H8-224790 A
Patent Literature 2: JP 2006-348214 A

SUMMARY OF INVENTION

Technical Problem

The resin composition for stereolithography disclosed in Patent Literature 1 is not specifically described with regard to its effectiveness in compositions that must contain inorganic particles, such as in dental materials. Ultraviolet absorbers have a tendency to produce a color in response to applied light; however, Patent Literature 1 is silent as to the shade. Patent Literature 2 describing a photocurable liquid composition for stereolithography does not describe anything about sedimentation of inorganic particles during storage, or the mechanical characteristics and the shade of the cured product.

It is accordingly an object of the present invention to provide a resin composition for stereolithography that is easily shapable with good shape precision by stereolithography while reducing sedimentation of inorganic particles during storage, and that enables production of a three-dimensional shaped article that, in addition to having a desirable shade and good shade stability, excels in mechanical characteristics such as flexural strength and flexural modulus.

Solution to Problem

Specifically, the present invention includes the following.
[1] A resin composition for stereolithography comprising a polymerizable monomer (a), a photopolymerization initiator (b), an inorganic particle (c) having an average particle diameter of 5 to 500 nm, and a hindered phenolic compound (d), wherein the content of the photopolymerization initiator (b) is 0.1 to 10 parts by mass relative to 100 parts by mass of the polymerizable monomer (a), the content of the inorganic particle (c) is 50 to 400 parts by mass relative to 100 parts by mass of the polymerizable monomer (a), and the content of the hindered phenolic compound (d) is 0.1 to 500 parts by mass relative to 100 parts by mass of the photopolymerization initiator (b).

[2] The resin composition for stereolithography according to [1], which has a consistency at 25° C. of 30 mm or more.

[3] The resin composition for stereolithography according to [1] or [2], wherein the inorganic particle (c) is surface-treated.

[4] The resin composition for stereolithography according to any one of [1] to [3], wherein the inorganic particle (c) comprises a spherical inorganic particle (c-1).

[5] The resin composition for stereolithography according to [4], wherein the spherical inorganic particle (c-1) has a sphericity of 0.70 to 0.99.

[6] The resin composition for stereolithography according to any one of [1] to [5], wherein the inorganic particle (c) has an average particle diameter of 7.5 to 300 nm.

[7] The resin composition for stereolithography according to any one of [1] to [6], wherein the inorganic particle (c) has an average particle diameter of 10 to 200 nm.

[8] The resin composition for stereolithography according to any one of [1] to [7], which comprises no inorganic particles other than the inorganic particle (c).

[9] The resin composition for stereolithography according to any one of [1] to [8], which further comprises an organic ultraviolet absorber (e).

[10] The resin composition for stereolithography according to any one of [1] to [9], wherein the polymerizable monomer (a) comprises an aromatic bifunctional polymerizable monomer.

[11] The resin composition for stereolithography according to [10], wherein the aromatic bifunctional polymerizable monomer is at least one selected from the group consisting of 2,2-bis[4-(3-methacryloyloxy-2-hydroxypropoxy)phenyl]propane, and 2,2-bis(4-(meth)acryloyloxypolyethoxyphenyl)propane.

[12] The resin composition for stereolithography according to any one of [1] to [11], wherein the polymerizable monomer (a) comprises a monofunctional monomer.

[13] The resin composition for stereolithography according to [12], wherein the monofunctional monomer comprises a (meth)acrylamide polymerizable monomer.

[14] The resin composition for stereolithography according to any one of [1] to [13], wherein the hindered phenolic compound (d) comprises a compound represented by the following general formula [I], and/or a compound represented by the following general formula [III],

[Chem. 1]

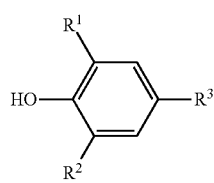

[I]

wherein $R^1$ to $R^3$ each independently represent an optionally substituted alkyl group having 1 to 20 carbon atoms, an optionally substituted alkoxy group having 1 to 20 carbon atoms, an optionally substituted aryl group having 6 to 12 carbon atoms, or a hydroxyl group, and the groups represented by $R^1$ to $R^3$ (excluding the hydroxyl group) may contain at least one binding group selected from the group consisting of —O—, —S—, —NH—, —N($R^4$)—, —O(CO)—, and —CO—, where $R^4$ represents an alkyl group having 1 to 6 carbon atoms,

[Chem. 2]

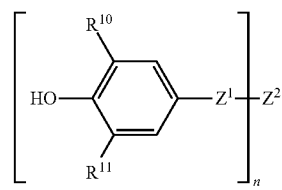

[III]

wherein $R^{10}$ and $R^{11}$ each independently represent an optionally substituted alkyl group having 1 to 20 carbon atoms, an optionally substituted alkoxy group having 1 to 20 carbon atoms, or an optionally substituted aryl group having 6 to 12 carbon atoms, $Z^1$ represents an optionally substituted alkylene group having 1 to 20 carbon atoms, $Z^2$ represents a carbon atom, an oxygen atom, a nitrogen atom, a sulfur atom, or an aryl group, n represents an integer of 2 to 6, and the groups represented by $R^{10}$, $R^{11}$, and $Z^1$ may contain at least one binding group selected from the group consisting of —O—, —S—, —NH—, —N($R^{12}$)—, —O(CO)—, and —CO—, where $R^{12}$ represents an alkyl group having 1 to 6 carbon atoms.

[15] The resin composition for stereolithography according to [14], wherein the hindered phenolic compound (d) comprises a compound represented by general formula [III].

[16] The resin composition for stereolithography according to [15], wherein the alkylene group represented by $Z^1$ in a compound represented by the general formula [III] is interrupted by at least one binding group selected from the group consisting of —O—, —S—, —NH—, —N($R^{12}$)—, —O(CO)—, and —CO—.

[17] The resin composition for stereolithography according to any one of [1] to [16], wherein the content of the hindered phenolic compound (d) is 5.0 to 100 parts by mass relative to 100 parts by mass of the photopolymerization initiator (b).

[18] A dental material comprising a cured product of a resin composition for stereolithography of any one of [1] to [17].

[19] A dental prosthesis comprising a cured product of a resin composition for stereolithography of any one of [1] to [17].

[20] A method for producing a three-dimensional shaped article by photo-solidification with a resin composition for stereolithography of any one of [1] to [17].

[21] The method according to [20], wherein the photo-solidification is bottom-up vat stereolithography.

Advantageous Effects of Invention

A resin composition for stereolithography of the present invention is easily shapable with good shape precision while reducing sedimentation of inorganic particles during storage, and enables production of a three-dimensional shaped article that, in addition to having a desirable shade and good shade stability, excels in mechanical characteristics such as flexural strength and flexural modulus. A resin composition for stereolithography of the present invention can be suitably used for various types of dental materials, particularly dental prostheses.

DESCRIPTION OF EMBODIMENTS

A resin composition for stereolithography of the present invention comprises a polymerizable monomer (a), a photopolymerization initiator (b), an inorganic particle (c) having an average particle diameter of 5 to 500 nm, and a hindered phenolic compound (d). In a resin composition for stereolithography of the present invention, the content of the photopolymerization initiator (b) is 0.1 to 10 parts by mass relative to 100 parts by mass of the polymerizable monomer (a), the content of the inorganic particle (c) is 50 to 400 parts by mass relative to 100 parts by mass of the polymerizable monomer (a), and the content of the hindered phenolic compound (d) is 0.1 to 500 parts by mass relative to 100 parts by mass of the photopolymerization initiator (b). A resin composition for stereolithography of the present invention has a shapable consistency, and can be easily shaped with excellent shape precision. A method of consistency measurement is as described in the EXAMPLES section below. In this specification, "consistency" is an index of how easily a resin composition for stereolithography spreads as measured by the method described in the EXAMPLES section below. Higher consistency values mean that a resin composition for stereolithography has higher fluidity and superior shapability, whereas lower consistency values mean that a resin composition for stereolithography is less fluid. In the present specification, the upper limits and lower limits of numeric ranges (for example, ranges of contents of components, ranges of values calculated from components, and numeric ranges of physical properties) can be combined appropriately. In the present specification, the term "stereolithography" is also referred to as "photo-solidification".

Polymerizable Monomer (a)

A radical polymerizable monomer is preferably used as the polymerizable monomer (a) used in a resin composition for stereolithography of the present invention. Specific examples of radical polymerizable monomers as polymerizable monomer (a) include (meth)acrylate polymerizable monomers; (meth)acrylamide polymerizable monomers; esters of acids such as α-cyanoacrylic acid, (meth)acrylic acid, α-halogenated acrylic acid, crotonic acid, cinnamic acid, sorbic acid, maleic acid, and itaconic acid; vinyl esters; vinyl ethers; mono-N-vinyl derivatives; and styrene derivatives. In view of curability, preferred are (meth)acrylate polymerizable monomers and (meth)acrylamide polymerizable monomers. These may be used alone, or two or more thereof may be used in combination. As used herein, "(meth)acryl" is meant to be inclusive of both "methacryl" and "acryl". The same applies to similar expressions, such as "(meth)acrylate" and "(meth)acryloyloxy".

Examples of the polymerizable monomer (a) in the present invention include a monofunctional monomer having one polymerizable group (hereinafter, also referred to simply as "monofunctional monomer"), and a polyfunctional monomer having a plurality of polymerizable groups (hereinafter, also referred to simply as "polyfunctional monomer"). Examples of the monofunctional monomer include monofunctional (meth)acrylate polymerizable monomers, and monofunctional (meth)acrylamide polymerizable monomers.

Examples of the monofunctional (meth)acrylate polymerizable monomers include 2-hydroxyethyl (meth)acrylate, 2-hydroxypropyl (meth)acrylate, 3-hydroxypropyl (meth)acrylate, 4-hydroxybutyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, methyl (meth)acrylate, ethyl (meth)acrylate, propyl (meth)acrylate, isopropyl (meth)acrylate, n-butyl (meth)acrylate, sec-butyl (meth)acrylate, t-butyl (meth)acrylate, isobutyl (meth)acrylate, n-hexyl (meth)acrylate, cyclohexyl (meth)acrylate, lauryl (meth)acrylate, cetyl (meth)acrylate, stearyl (meth)acrylate, isobornyl (meth)acrylate, benzyl (meth)acrylate, phenyl (meth)acrylate, 2,3-dibromopropyl (meth)acrylate, 3-(meth)acryloyloxypropyltrimethoxysilane, and 11-(meth)acryloyloxyundecyltrimethoxysilane. Examples of the monofunctional (meth)acrylamide polymerizable monomers include N-(meth)acryloylmorpholine, N,N-dimethyl(meth)acrylamide, N,N-diethyl(meth)acrylamide, N,N-di-n-propyl(meth)acrylamide, N,N-di-n-butyl(meth)acrylamide, N,N-di-n-hexyl(meth)acrylamide, N,N-di-n-octyl(meth)acrylamide, N,N-di-2-ethylhexyl(meth)acrylamide, N-hydroxyethyl(meth)acrylamide, and N,N-bis(2-hydroxyethyl)acrylamide. These may be used alone, or two or more thereof may be used in combination. In view of superior curability and providing high shape precision when combined with a polyfunctional monomer, preferred are (meth)acrylamide polymerizable monomers, more preferably N-(meth)acryloylmorpholine, N,N-dimethyl(meth)acrylamide, and N, N-diethyl(meth)acrylamide.

Examples of the polyfunctional monomer include aromatic bifunctional polymerizable monomers, aliphatic bifunctional polymerizable monomers, and tri- and higher-functional polymerizable monomers.

Examples of the aromatic bifunctional polymerizable monomers include 2,2-bis((meth)acryloyloxyphenyl)propane, 2,2-bis[4-(3-acryloyloxy)-2-hydroxypropoxyphenyl]propane, 2,2-bis[4-(3-methacryloyloxy-2-hydroxypropoxy)phenyl]propane (commonly known as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl)pyromellitate. These may be used alone, or two or more thereof may be used in combination. In view of superior curability and superior mechanical strength of the cured product, preferred are 2,2-bis[4-(3-methacryloyloxy-2-hydroxypropoxy)phenyl]propane, and 2,2-bis(4-(meth)acryloyloxypolyethoxyphenyl)propane, the latter being more preferably 2,2-bis(4-methacryloyloxypolyethoxyphenyl)propane (a compound with an average number of moles of ethoxy group added of 2.6; commonly known as "D-2.6E").

Examples of the aliphatic bifunctional polymerizable monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, 1,2-bis(3-methacryloyloxy-2-hydroxypropoxy)ethane, 2,2,4-trimethylhexamethylene bis(2-carbamoyloxyethyl)dimethacrylate (commonly known as "UDMA"), and N-methacryloyloxyethylacrylamide. In view of superior curability and superior mechanical strength of the cured product, preferred is 2,2,4-trimethyl-hexamethylene bis(2-carbamoyloxyethyl)dimethacrylate. These may be used alone, or two or more thereof may be used in combination.

Examples of the tri- and higher-functional polymerizable monomers include trimethylolpropane tri(meth)acrylate, trimethylolethane tri(meth)acrylate, trimethylolnethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetra(meth)acrylate, 1,7-diacryloyloxy-2,2,6,6-tetra(meth)acryloyloxymethyl-4-oxaheptane, and N,N',N'',N'''-tetra(meth)acryloyltriethyltetramine. In view of superior curability and superior mechanical strength of the cured product, preferred are N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxaheptane. These may be used alone, or two or more thereof may be used in combination.

When the polymerizable monomer (a) comprises a monofunctional (meth)acrylate polymerizable monomer, the content of the monofunctional (meth)acrylate polymerizable monomer is preferably 10 to 55 mass %, more preferably 15 to 50 mass %, even more preferably 15 to 45 mass % in total 100 mass % of polymerizable monomer (a). In view of superior curability and superior mechanical strength of the cured product, the content of a bifunctional (meth)acrylate polymerizable monomer of when the polymerizable monomer (a) comprises a bifunctional(meth)acrylate polymerizable monomer is preferably 50 mass % or more, more preferably 60 mass % or more, even more preferably 70 mass % or more in total 100 mass % of polymerizable monomer (a). In the present specification, the content of a polymerizable monomer in total 100 mass % of polymerizable monomer (a) means the content (mass) of the polymerizable monomer of when the total amount of the polymerizable monomer (a) present is converted to 100 mass %.

The content of polymerizable monomer (a) is preferably 15 to 70 mass %, more preferably 20 to 65 mass %, even more preferably 25 to 60 mass % of the whole resin composition for stereolithography.

Photopolymerization Initiator (b)

The photopolymerization initiator (b) used in the present invention may be selected from photopolymerization initiators used in industry, preferably from photopolymerization initiators used in dentistry.

Examples of the photopolymerization initiator (b) include (bis)acylphosphine oxides and salts thereof, thioxanthones and quaternary ammonium salts thereof, ketals, α-diketones, coumarins, anthraquinones, benzoin alkyl ether compounds, and α-aminoketone compounds. These may be used alone, or two or more thereof may be used in combination.

Preferably, the photopolymerization initiator (b) is at least one selected from the group consisting of (bis)acylphosphine oxides and salts thereof, and α-diketones. In this way, a resin composition for stereolithography can be obtained that has excellent photocurability both in the ultraviolet and visible regions, and that shows sufficient photocurability even when the light source is a laser (e.g., an Ar laser, a He—Cd laser), or a lighting such as a halogen lamp, a xenon lamp, a metal halide lamp, a light emitting diode (LED), a mercury lamp, or a fluorescent lamp.

Examples of acylphosphine oxides and salts thereof in the (bis)acylphosphine oxides and salts thereof used as the photopolymerization initiator (b) include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2,6-dimethylphenyl)phosphonate, sodium salts of 2,4,6-trimethylbenzoylphenylphosphine oxide, potassium salts of 2,4,6-trimethylbenzoyldiphenylphosphine oxide, and ammonium salts of 2,4,6-trimethylbenzoyldiphenylphosphine oxide. Examples of bisacylphosphine oxides and salts thereof include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl) phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphine oxide, and salts of these (such as alkali metal salts, alkali-earth metal salts, and ammonium salts). Other examples include compounds mentioned in JP 2000-159621 A.

Among these (bis)acylphosphine oxides, particularly preferred are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of α-diketones used as the photopolymerization initiator (b) include diacetyl, benzyl, camphorquinone, 2,3-pentadione, 2,3-octadione, 9,10-phenanthrenequinone, 4,4'-oxybenzyl, and acenaphthenequinone. Camphorquinone is particularly preferred when the light source used is a visible light source.

In view of curability and other properties of the resin composition for stereolithography obtained, the content of the photopolymerization initiator (b) in a resin composition for stereolithography of the present invention is preferably 0.1 to 10 parts by mass, more preferably 0.5 to 7.5 parts by mass, even more preferably 1.0 to 5.0 parts by mass relative to 100 parts by mass of polymerizable monomer (a). When the content of photopolymerization initiator (b) is more than 10 parts by mass relative to 100 parts by mass of polymerizable monomer (a), the photopolymerization initiator (b) may precipitate out of the resin composition for stereolithography when the solubility of the photopolymerization initiator itself is low.

Inorganic Particle (c)

Examples of the inorganic particle (c) used in the present invention include quartz, silica, titanium oxide, zirconium oxide (zirconia), zinc oxide, cerium oxide, aluminum oxide (alumina), silica-titania, silica-titania-barium oxide, silica-zirconia, silica-alumina, barium glass, aluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone, or two or more thereof may be used in combination. In view of superior mechanical strength of a cured product of the resin composition for stereolithography obtained, preferred for use are quartz, silica, alumina, zirconia, barium glass, and fluoroaluminosilicate glass, more preferably silica and barium glass, even more preferably barium glass.

In view of shape precision and reduced sedimentation, the inorganic particle (c) needs to have an average particle diameter of 5 to 500 nm. The average particle diameter of inorganic particle (c) is preferably 7.5 to 300 nm, more preferably 10 to 200 nm, even more preferably 12.5 to 100 nm. When the average particle diameter of inorganic particle (c) is less than 5 nm, the viscosity of the resin composition for stereolithography increases, and the shape precision tends to decrease. When the average particle diameter of inorganic particle (c) is more than 500 nm, the shape precision tends to decrease as a result of increased scattering of applied light, and sedimentation of inorganic particle (c) becomes more likely to occur during storage or shaping.

The shape of inorganic particle (c) is not particularly limited. However, the inorganic particle (c) preferably comprises a spherical inorganic particle (c-1) because such particles improve shape precision by providing superior fluidity and allowing easy recovery of a liquid level in the vicinity of the shaped article being shaped. The spherical inorganic particle (c-1) has a sphericity of preferably 0.70 to 0.99, more preferably 0.80 to 0.99, even more preferably 0.90 to 0.99.

The shape of inorganic particle (c) can be measured from a captured image of inorganic particle (c) taken with a scanning electron microscope (hereinafter, "SEM"). The average particle diameter and sphericity can be determined by processing a SEM image with an image analyzer. At least 200 samples are chosen for image processing, and a mean value is used. Here, "sphericity" is defined as a roundness determined by image processing of an image captured with a SEM. Roundness is represented by the following expression. A roundness of 1 represents a true circle.

$$\text{Roundness} = (4 \cdot \pi \cdot S)/(L^2)$$

where S represents the area of particles after image processing, and L represents the particle circumference.

The particle diameter used for the calculation of roundness is the diameter of a corresponding circle (the diameter of when the particle is assumed as a true circle; $(4 \cdot S/\pi)^{1/2}$).

For shapes of inorganic particle (c) other than a sphere, the particle diameter can be determined in the same fashion by capturing and processing an image. In this case, however, the particle diameter is determined as an arithmetic mean value of the maximum and minimum lengths of particles, and the average primary particle diameter is calculated from the number of particles and the particle diameter.

In view of the consistency of the resin composition for stereolithography obtained, and the shape precision and mechanical characteristics of the cured product, the content of the inorganic particle (c) in a resin composition for stereolithography of the present invention needs to be 50 to 400 parts by mass relative to 100 parts by mass of polymerizable monomer (a). The content of inorganic particle (c) is preferably 75 to 300 parts by mass, more preferably 100 to 200 parts by mass. A three-dimensional shaped article of a resin composition for stereolithography of the present invention cannot have sufficient mechanical characteristics when the content of inorganic particle (c) is less than 50 parts by mass relative to 100 parts by mass of polymerizable monomer (a). When the content of inorganic particle (c) is more than 400 parts by mass relative to 100 parts by mass of polymerizable monomer (a), the fluidity of the resin composition for stereolithography decreases, and causes difficulty in shaping.

In order to adjust miscibility with polymerizable monomer (a), the inorganic particle (c) is preferably surface-treated beforehand with a known surface treatment agent such as an acidic group-containing organic compound; a fatty acid amide such as a saturated fatty acid amide, an unsaturated fatty acid amide, a saturated fatty acid bisamide, or an unsaturated fatty acid bisamide; or an organosilicon compound such as a silane coupling agent. In order to improve the mechanical strength of the cured product through increased chemical bonding between polymerizable monomer (a) and inorganic particle (c), the inorganic particle (c) is preferably surface-treated with an acidic group-containing organic compound. Examples of the acidic group-containing organic compound include an organic compound having at least one acidic group such as a phosphoric acid group, a pyrophosphoric acid group, a thiophosphoric acid group, a phosphonic acid group, a sulfonic acid group, and a carboxylic acid group. The organic compound is preferably one having at least one phosphoric acid group. When two or more surface treatment agents are used, the surface treatment agent layer may be a mixture of two or more surface treatment agents, or may have a laminate structure with multiple layers of surface treatment agents.

Examples of acidic group-containing organic compounds containing a phosphoric acid group include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, and ammonium salts of these.

As an example, preferred for use as acidic group-containing organic compounds having an acidic group such as a pyrophosphoric acid group, a thiophosphoric acid group, a phosphonic acid group, a sulfonic acid group, or a carboxylic acid group are those mentioned in WO2012/042911.

Examples of the saturated fatty acid amide include palmitamide, stearamide, and behenamide. Examples of the unsaturated fatty acid amide include oleamide and erucamide. Examples of the saturated fatty acid bisamide include ethylenebispalmitamide, ethylenebisstearamide, and hexamethylenebisstearamide. Examples of the unsaturated fatty acid bisamide include ethylenebisoleamide, hexamethylenebisoleamide, and N,N'-dioleylsebacamide.

Examples of the organosilicon compound include compounds represented by $R^{13}{}_m SiW_{4-m}$. In the formula, $R^{13}$ is a substituted or unsubstituted hydrocarbon group having 1 to 12 carbon atoms, W represents a C1 to C4 alkoxy group, a hydroxyl group, a halogen atom, or a hydrogen atom, and m is an integer of 0 to 3. Here, $R^{13}$ and W each may be the same or different from each other when a plurality of $R^{13}$ or W exists.

Specific examples include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(βmethoxyethoxy)silane, 3,3,3-trifluoropropyltrimethoxysilane, methyl-3,3,3-trifluoropropyldimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyldiethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloyloxyalkyltrimethoxysilane [3 to 12 carbon atoms between the (meth)acryloyloxy group and the silicon atom; e.g., γ-methacryloyloxypropyltrimethoxysilane], ω-(meth)acryloyloxyalkyltriethoxysilane [3 to 12 carbon atoms between the (meth) acryloyloxy group and the silicon atom; e.g., γ-methacryloyloxypropyltriethoxysilane], hexaethyldisilazane, hexa-n-propyldisilazane, hexaisopropyldisilazane, 1,1,2,2-tetramethyl-3,3-diethyldisilazane, 1,1,3,3-tetramethyldisilazane, 1,1,1,3,3,3-hexamethyldisilazane, and 1,1,1,3,3-pentamethyldisilazane.

Preferred are silane coupling agents having a functional group that is copolymerizable with the polymerizable monomer. Examples include ω-(meth)acryloyloxyalkyltrimethoxysilane [3 to 12 carbon atoms between the (meth)acryloyloxy group and the silicon atom], ω-(meth)acryloyloxyalkyltriethoxysilane [3 to 12 carbon atoms between the (meth)acryloyloxy group and the silicon atom], vinyltrimethoxysilane, vinyltriethoxysilane, vinyltriacetoxysilane, and γ-glycidoxypropyltrimethoxysilane.

The surface treatment may be achieved using any known surface treatment method, including, for example, a method that adds the surface treatment agent by spraying while vigorously stirring the inorganic particle (c), and a method that disperses or dissolves inorganic particle (c) and the surface treatment agent in a suitable solvent, and removes the solvent.

The amount of the surface treatment agent used is not particularly limited, and is, for example, preferably 0.1 to 50 parts by mass relative to 100 parts by mass of inorganic particle (c).

A resin composition for stereolithography of the present invention may consist essentially of spherical inorganic particle (c-1) as inorganic particle (c). The content of spherical inorganic particle (c-1) is preferably 60 to 100 mass %, more preferably 80 to 100 mass %, even more preferably 90 to 100 mass % in 100 mass % of inorganic particle (c).

Hindered Phenolic Compound (d)

A resin composition for stereolithography of the present invention comprises a hindered phenolic compound (d). In a resin composition for stereolithography of the present invention, the hindered phenolic compound (d) is used to reduce coloring of a cured product of the resin composition for stereolithography, and discoloration of a cured product of the resin composition for stereolithography during storage.

A phenolic compound is generally added as a polymerization inhibitor or an antioxidant to provide storage stability to a resin composition. The present invention uses a hindered phenolic compound to reduce coloring and discoloration (particularly, yellowing) due to exposure to an active energy beam, such as a ultraviolet laser, emitted by a stereolithography device. The phenolic compound used in the present invention must be a hindered phenolic compound because a hindered phenolic compound interferes little with curing, and is highly effective at reducing coloring and discoloration of the cured product. The easy shapability of a resin composition for stereolithography of the present invention is achievable, and coloring and discoloration (particularly, yellowing) of the cured product can be reduced only when the hindered phenolic compound (d) is contained in specific proportions with respect to the photopolymerization initiator (b).

Examples of the hindered phenolic compound (d) include compounds represented by the following general formula [I], compounds represented by the following general formula [II], and compounds represented by the following general formula [III]. Preferred are compounds represented by general formula [I], and compounds represented by general formula [III].

[Chem. 3]

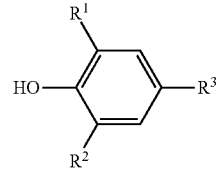

[I]

wherein $R^1$ to $R^3$ each independently represent an optionally substituted alkyl group having 1 to 20 carbon atoms, an optionally substituted alkoxy group having 1 to 20 carbon atoms, an optionally substituted aryl group having 6 to 12 carbon atoms, or a hydroxyl group, and the groups represented by $R^1$ to $R^3$ (excluding the hydroxyl group) may contain at least one binding group selected from the group consisting of —O—, —S—, —NH—, —N($R^4$)—, —O(CO)—, and —CO—, where $R^4$ represents an alkyl group having 1 to 6 carbon atoms,

[Chem. 4]

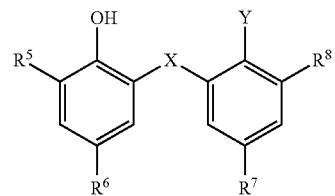

[II]

wherein $R^5$ to $R^8$ each independently represent an optionally substituted alkyl group having 1 to 20 carbon atoms, an optionally substituted alkoxy group having 1 to 20 carbon atoms, an optionally substituted aryl group having 6 to 12 carbon atoms, or a hydroxyl group, X represents an optionally substituted alkylene group having 1 to 20 carbon atoms, Y represents a vinyloxy group or a (meth)acryloyloxy group, and the groups represented by $R^5$ to $R^8$ and X (excluding the hydroxyl group) may contain at least one binding group selected from the group consisting of —O—, —S—, —NH—, —N($R^9$)—, —O(CO)—, and —CO—, where $R^9$ represents an alkyl group having 1 to 6 carbon atoms.

[Chem. 5]

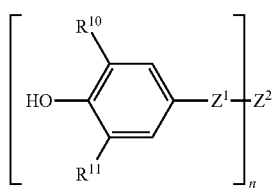

[III]

wherein $R^{10}$ and $R^{11}$ each independently represent an optionally substituted alkyl group having 1 to 20 carbon atoms, an optionally substituted alkoxy group having 1 to 20 carbon atoms, or an optionally substituted aryl group having 6 to 12 carbon atoms, $Z^1$ represents an optionally substituted alkylene group having 1 to 20 carbon atoms, $Z^2$ represents a carbon atom, an oxygen atom, a nitrogen atom, a sulfur atom, or an aryl group, n represents an integer of 2 to 6, and the groups represented by $R^{10}$, $R^{11}$, and $Z^1$ may contain at least one binding group selected from the group consisting of —O—, —S—, —NH—, —N($R^{12}$)—, —O(CO)—, and —CO—, where $R^{12}$ represents an alkyl group having 1 to 6 carbon atoms.

The C1 to C20 alkyl group represented by $R^1$ to $R^3$ and $R^5$ to $R^8$ may be linear or branched. The alkyl group may be, for example, methyl, ethyl, n-propyl, isopropyl, n-butyl, isobutyl, sec-butyl, 2-methylpropyl, tert-butyl, n-pentyl, isopentyl, sec-pentyl, neopentyl, 1-ethylpropyl, 1,1-dimethylpropyl, n-hexyl, 1-methylpentyl, 1-ethylbutyl, 2-ethylbutyl, 1,1-dimethylbutyl, n-heptyl, 2-methylhexyl, n-octyl, isooctyl, tert-octyl, n-nonyl, n-decyl, 1-methylnonyl, n-undecyl, or n-dodecyl. The alkyl group represented by $R^1$ to $R^3$ and $R^5$ to $R^8$ may be unsubstituted. The alkyl group represented by $R^1$ to $R^3$ and $R^5$ to $R^8$ has preferably 1 to 10 carbon atoms. In view of the superior effect to reduce coloring and discoloration, the number of carbon atoms is more preferably 1 to 6. The C1 to C20 alkoxy group represented by $R^1$ to $R^3$ and $R^5$ to $R^8$ may be linear or branched. The alkoxy group may be, for example, methoxy, ethoxy, n-propoxy, isopropoxy, n-butoxy, sec-butoxy, tert-butoxy, n-pentyloxy, isopentyloxy, or n-hexyloxy. The alkoxy group represented by $R^1$ to $R^3$ and $R^5$ to $R^8$ may be unsubstituted. The alkoxy group represented by $R^1$ to $R^7$ has preferably 1 to 10 carbon atoms. In view of the superior effect to reduce coloring and discoloration, the number of carbon atoms is more preferably 1 to 6. The C6 to C12 aryl group represented by $R^1$ to $R^3$ and $R^5$ to $R^8$ may be, for example, phenyl, benzyl, or naphthyl. The aryl group has preferably 6 to 10 carbon atoms. Examples of the substituents of the alkyl group, alkoxy group, and aryl group represented by $R^1$ to $R^3$ and $R^5$ to $R^8$ include a linear or branched alkyl group having 1 to 10 carbon atoms, a halogen atom (a fluorine atom, a chlorine atom, a bromine atom, or an iodine atom), and a carboxy group. Examples of the alkyl group represented by $R^4$ and $R^9$ include the same C1 to C6 alkyl groups represented by $R^1$ to $R^3$ and $R^5$ to $R^8$. The C1 to C20 alkylene group represented by X may be linear or branched, and may be, for example, methylene, methylmethylene, ethylene, n-propylene, isopropylene, n-butylene, 1-methylbutylene, n-pentylene, 1,1-dimethylpropylene, n-hexylene, n-heptylene, n-octylene, n-nonylene, or n-decylene. The alkylene group represented by X has preferably 1 to 10 carbon atoms. In view of the superior effect to reduce coloring and discoloration, the number of carbon atoms is more preferably 1 to 6, even more preferably 1 to 4. Y is preferably a (meth)acryloyloxy group, more preferably an acryloyloxy group. A certain preferred embodiment is, for example, a resin composition for stereolithography in which the hindered phenolic compound (d) comprises compounds represented by general formula [I], and the groups represented by $R^1$ to $R^3$ do not contain the binding group —O—, —S—, —NH—, —N($R^4$)—, —O(CO)—, or —CO—.

The alkyl group, alkoxy group, and aryl group represented by $R^{19}$ and $R^{11}$ may be the same alkyl group, alkoxy group, and aryl group represented by $R^1$ to $R^3$ and $R^5$ to $R^8$. $R^{10}$ and $R^{11}$ are preferably alkyl groups. In view of the superior effect to reduce coloring and discoloration, $R^{19}$ and $R^{11}$ are more preferably branched alkyl groups, even more preferably branched alkyl groups having 3 to 6 carbon atoms. The alkyl group represented by $R^{12}$ may be the same alkyl group represented by $R^4$ and $R^9$. The alkylene group represented by $Z^1$ may be the same alkylene group represented by X. $Z^2$ represents a carbon atom, an oxygen atom, a nitrogen atom, a sulfur atom, or an aryl group, and is preferably a carbon atom, a sulfur atom, or an aryl group. The aryl group represented by $Z^2$ may be the same aryl group represented by $R^1$ to $R^3$ and $R^5$ to $R^8$, and is preferably a phenyl group, more preferably a substituted phenyl group, even more preferably a substituted phenyl group substituted with a C1 to C3 alkyl group. n represents an integer of 2 to 6, preferably an integer of 2 to 4. n is appropriately selected according to the number of bonds in $Z^2$. Another preferred embodiment is, for example, a resin composition for stereolithography in which the hindered phenolic compound (d) comprises compounds represented by general formula [III], and the alkylene group represented by $Z^1$ contains at least one binding group selected from the group consisting of —O—, —S—, —NH—, —N($R^{12}$)—, —O(CO)—, and —CO—. The hindered phenolic compound in such an embodiment is preferably one in which the alkylene group represented by $Z^1$ contains at least one binding group selected from the group consisting of —O—, —O(CO)—, and —CO—, more preferably one in which $Z^1$ is a C1 to C6 alkylene group, and the alkylene group contains at least one binding group selected from the group consisting of —O—, —O(CO)—, and —CO—, even more preferably one in which $Z^1$ is a C1 to C6 alkylene group, and the alkylene group contains at least one binding group selected from the group consisting of —O—, —O(CO)—, and —CO—, and in which $Z^2$ is a carbon atom, and n is 4. In the present specification, a group (for example, an alkylene group) being interrupted by a specific binding group means that the binding group is present in the middle of the group (for example, an alkylene group), and these are synonymous. For example, $Z^1$ means —$CH_2$—O—$CH_2$— when the alkylene group represented by $Z^1$ is an ethylene group and containing —O—.

Examples of the hindered phenolic compound (d) include 3,5-di-t-butyl-4-hydroxytoluene, 3,5-di-t-butyl-4-hydroxyanisole, 2,6-di-t-butyl-4-hydroxytoluene, 2,6-di-t-butyl-4- hydroxyanisole, 4-t-butylpyrocatechol, pentaerythritol tetrakis[3-(3,5-di-t-butyl-4-hydroxyphenyl)propionate], thiodiethylene bis[3-(3,5-di-t-butyl-4-hydroxyphenyl)propionate], octadecyl-3-(3,5-di-t-butyl-4-hydroxyphenyl)propionate, N,N'-hexane-1,6-diylbis(3-(3,5-di-t-butyl-4-hydroxyphenylpropionamide)), octyl 3-(3,5-di-tert-butyl-4-hydroxyphenyl)propanoate (IRGANOX 1135), 3,3',3",5,5', 5"-hexa-t-butyl-α,α',α"-(mesitylene-2,4,6-tolyl)tri-p-cresol, and 4,6-bis(octylthiomethyl)-o-cresol. Preferred is 3,5-di-t-butyl-4-hydroxytoluene for its strong effect to reduce discoloration while showing a weak curing inhibitory effect.

The content of the hindered phenolic compound (d) in the resin composition for stereolithography must be 0.1 to 500 parts by mass relative to 100 parts by mass of photopolymerization initiator (b). The content of hindered phenolic compound (d) is preferably 0.5 to 300 parts by mass, more preferably 1.0 to 200 parts by mass, even more preferably 5.0 to 100 parts by mass, most preferably 10 to 50 parts by mass. With 0.1 to 500 parts by mass of hindered phenolic compound (d), it is possible to desirably maintain curability, shade, and shade stability. When the content of hindered phenolic compound (d) is less than 0.1 parts by mass relative to 100 parts by mass of photopolymerization initiator (b), a formed article of the resin composition for stereolithography tends to turn yellow, and show inferior shades and inferior shade stability. When the content of hindered phenolic compound (d) is more than 500 parts by mass relative to 100 parts by mass of photopolymerization initiator (b), the mechanical strength of the formed article tends to decrease as a result of a reduced degree of polymerization in shaping the resin composition for stereolithography. Particularly, in vat stereolithography, shaping of the resin composition becomes difficult to achieve as a result of detachment or shape discontinuity due to improper curing.

Organic Ultraviolet Absorber (e)

For further improvement of shape precision, a resin composition for stereolithography of the present invention preferably comprises an organic ultraviolet absorber (e).

Examples of the organic ultraviolet absorber (e) include benzotriazole compounds, benzophenone compounds, and thiophene compounds. Preferred as benzotriazole compounds are compounds having a hydroxyl group bound at position 2 of the aromatic ring attached to nitrogen atoms of the triazole structure. More preferred for even greater improvement of shape precision are compounds having a hydroxyl group bound at position 2 of the aromatic ring attached to nitrogen atoms of the triazole structure, and having a C1 to C10 alkyl group at position 3 and/or position 5 of the aromatic ring. Examples of the benzotriazole compounds include 2-(2-hydroxy-5-methylphenyl)benzotriazole (TINUVIN P), 2-(2-hydroxy-5-tert-octylphenyl)benzotriazole (TINUVIN 329), 2-(2'-hydroxy-3',5'-d i-tert-butylphenyl)benzotriazole, 2-(2'-hydroxy-5'-tert-butylphenyl)benzotriazole, 2-(2'-hydroxy-3'-tert-butyl-5'-methylphenyl)benzotriazole, 2-(2'-hydroxy-3',5'-d i-tert-amylphenyl)benzotriazole, 2-(2'-hydroxy-3'-tert-butyl-5'-methylphenyl)benzotriazole, 2-(2'-hydroxy-3'-tert-butyl-5'-methylphenyl)-5-chlorobenzotriazole, and 2-(2'-hydroxy-3', 5'-di-tert-butylphenyl)-5-chlorobenzotriazole. Examples of the benzophenone compounds include 2,4-dihydroxybenzophenone, 2-hydroxy-4-methoxybenzophenone, 2-hydroxy-4-n-octoxybenzophenone, 2-hydroxy-4-(dodecyloxy)benzophenone, 2-hydroxy-4-(octadecyloxy)benzophenone, 2,2'-dihydroxy-4-methoxybenzophenone, and 2,2'-dihydroxy-4, 4'-dimethoxybenzophenone. Examples of the thiophene compounds include thiophene compounds such as 2,5-bis (5-t-butyl-2-benzooxazolyl)thiophene. In view of providing more desirable shape precision, preferred are benzotriazole compounds.

The organic ultraviolet absorber (e) may be used alone, or two or more thereof may be used in combination. The content of organic ultraviolet absorber (e) ranges preferably from 0.001 to 10 parts by mass, more preferably 0.01 to 5 parts by mass, even more preferably 0.02 to 2 parts by mass relative to 100 parts by mass of polymerizable monomer (a).

A resin composition for stereolithography of the present invention is not particularly limited, as long as it comprises the polymerizable monomer (a), the photopolymerization initiator (b), the inorganic particle (c), and the hindered phenolic compound (d). Optionally, a resin composition for stereolithography of the present invention may comprise the organic ultraviolet absorber (e). For example, a resin composition for stereolithography of the present invention may comprise components other than these components. The content of such other components (components other than polymerizable monomer (a), photopolymerization initiator (b), inorganic particle (c), hindered phenolic compound (d), and, optionally, organic ultraviolet absorber (e)) in the resin composition for stereolithography may be less than 3 mass %, less than 2 mass %, less than 1 mass %, or 0 mass % relative to the whole resin composition for stereolithography. A certain preferred embodiment is, for example, a resin composition for stereolithography that comprises a polymerizable monomer (a), a photopolymerization initiator (b), an inorganic particle (c), a hindered phenolic compound (d), and, optionally, an organic ultraviolet absorber (e), and in which the inorganic particle (c) has an average particle diameter of 7.5 to 300 nm, and an inorganic particle (f), different from the inorganic particle (c), is absent. The inorganic particle (f) is not particularly limited, and may be, for example, a metal oxide particle (f-1) having an average particle diameter of 0.5 μm or more. The average particle diameter of inorganic particle (f) may vary according to the average particle diameter of inorganic particle (c), and may be 0.4 μm or more, or 0.3 μm or more. The metal oxide particle (f-1) is not particularly limited, and may be, for example, at least one selected from the group consisting of titanium oxide, aluminum oxide, zirconium oxide, zinc oxide, and cerium oxide. A resin composition for stereolithography of the present invention can be produced according to a known method.

In order to improve photocurability, a resin composition for stereolithography of the present invention may comprise a polymerization accelerator, provided that it is not detrimental to the intent and purpose of the present invention. Examples of the polymerization accelerator include amine compounds such as ethyl 4-(N,N-dimethylamino)benzoate, methyl 4-(N,N-dimethylamino)benzoate, n-butoxyethyl 4-(N,N-dimethylamino)benzoate, 2-(methacryloyloxy)ethyl 4-N,N-dimethylaminobenzoate, 4-(N,N-dimethylamino) benzophenone, and butyl 4-(N,N-dimethylamino)benzoate. In view of imparting superior curability to the resin composition for stereolithography, preferred is at least one selected from the group consisting of ethyl 4-(N,N-dimethylamino)benzoate, n-butoxyethyl 4-(N,N-dimethylamino) benzoate, and 4-(N,N-dimethylamino)benzophenone.

A resin composition for stereolithography of the present invention may comprise a known stabilizer, in order to inhibit property deterioration or to adjust photocurability. Examples of such stabilizers include polymerization inhibitors and antioxidants (the stabilizers exclude the hindered phenolic compound (d)). A certain embodiment is, for example, a resin composition for stereolithography that does not comprise a polymerization inhibitor or an antioxidant other than the hindered phenolic compound (d).

A resin composition for stereolithography of the present invention may comprise a known additive, in order to adjust shades or paste properties. Examples of such additives include pigments, dyes, organic solvents, and thickeners.

A resin composition for stereolithography of the present invention is easily shapable with good shape precision while reducing sedimentation of inorganic particles during storage, and a obtained three-dimensional shaped article thereby excels in mechanical characteristics such as flexural strength and flexural modulus, in addition to having a desirable shade and good shade stability. This makes a resin composition for stereolithography of the present invention usable in applications where such advantages can be exploited. Specifically, for example, a resin composition for stereolithography of the present invention can be used for various types of three-dimensional shaped article produced by photo-solidification curing. A cured product (three-dimensional shaped article) of a resin composition for stereolithography of the present invention can be suitably used as dental materials, most suitably as dental prostheses.

Another embodiment of the present invention is a method for producing a three-dimensional shaped article (for example, a dental material, particularly preferably a dental prosthesis) by a conventionally known stereolithography method (for example, bottom-up vat stereolithography) using any of the resin compositions for stereolithography described above.

Any known stereolithography method (for example, bottom-up vat stereolithography) and device (for example, a stereolithography device such as the DIGITALWAX® 028J-Plus manufactured by DWS) may be used when performing a known photo-solidification method (for example, bottom-up vat stereolithography) with a resin composition for stereolithography of the present invention. In the present invention, the light energy used to cure the resin is preferably an active energy beam. In the present invention, "active energy beam" means an energy ray capable of curing a resin composition for stereolithography, and includes, for example, ultraviolet light, an electron beam, X-rays, radiant rays, and high-frequency waves. For example, the active energy beam may be ultraviolet light of 300 to 400 nm wavelengths. The light source of active energy beam may be, for example, a laser such as an Ar laser or a He—Cd laser; or a lighting such as a halogen lamp, a xenon lamp, a metal halide lamp, an LED, a mercury lamp, or a fluorescent lamp. Lasers are particularly preferred. When the light source is a laser, the fabrication time can be reduced by increasing the energy level, and a three-dimensional shaped article of high shape precision can be obtained by taking advantage of the desirable convergence of a laser beam.

Photo-solidification using a resin composition for stereolithography of the present invention may use any known method (for example, bottom-up vat stereolithography) and any known stereolithography system, and the method and device are not particularly limited, as noted above. However, a typical example of a photo-solidification method preferred for use in the present invention is a method that produces a desired three-dimensional shaped article through a repeated procedure that includes a step of forming a cured layer by selectively applying an active energy beam to the resin composition for stereolithography so as to obtain a cured layer having a desired pattern, and a step of continuously forming another cured layer on the previously formed cured layer by similarly applying an active energy beam to a newly supplied, uncured liquid of the resin composition for stereolithography. The resulting three-dimensional shaped article may be used as it is, or may be used after improving mechanical characteristics, shape stability, or other properties by, for example, post-curing the product under applied light or heat.

The present invention encompasses embodiments combining the foregoing features, provided that the present invention can produce its effects with such combinations made in various forms within the technical idea of the present invention.

EXAMPLES

The following describes the present invention in greater detail by way of Examples. It should be noted, however, that the present invention is in no way limited by the following Examples, and various changes may be made by a person with ordinary skill in the art within the technical idea of the present invention. The components used for the resin compositions for stereolithography according to Examples and Comparative Examples are presented below, along with the abbreviations used.

Polymerizable Monomer (a)
    UDMA: 2,2,4-Trimethylhexamethylene bis(2-carbamoyloxyethyl)dimethacrylate (manufactured by Kyoeisha Chemical Co., Ltd.)
    Bis-GMA: 2,2-Bis[4-(3-methacryloyloxy-2-hydroxypropoxy)phenyl]propane (manufactured by Shin-Nakamura Chemical Co., Ltd.)
    TEGDMA: Triethylene glycol dimethacrylate (manufactured by Shin-Nakamura Chemical Co., Ltd.)
    ACMO: N-Acryloylmorpholine (manufactured by KJ Chemicals Corporation)

Photopolymerization Initiator (b)
    TPO: 2,4,6-Trimethylbenzoyldiphenylphosphine oxide Inorganic Particle (c)
    Inorganic particle (c)-1: γ-Methacryloyloxypropyltrimethoxysilane-treated spherical silica microparticle Admanano® YA050C (manufactured by Admatechs; average particle diameter: 50 nm; sphericity: 0.97)
    Inorganic particle (c)-2: γ-Methacryloyloxypropyltrimethoxysilane-treated spherical silica microparticle Admanano® YC100C (manufactured by Admatechs; average particle diameter: 100 nm; sphericity: 0.98)
    Inorganic particle (c)-3: γ-Methacryloyloxypropyltrimethoxysilane-treated spherical silica microparticle Admafine® SO-C1 (manufactured by Admatechs; average particle diameter: 300 nm; sphericity: 0.96)

Inorganic Particles Other than Inorganic Particle (c)
Inorganic Particle (Large Particle Diameter):
    γ-Methacryloyloxypropyltrimethoxysilane-treated spherical silica particle Admafine® SO-C4 (manufactured by Admatechs; average particle diameter: 1.0 μm)

Hindered Phenolic Compound (d)
    BHT: 3,5-Di-t-butyl-4-hydroxytoluene
    PETBHPP: Pentaerythritol tetrakis[3-(3,5-di-t-butyl-4-hydroxyphenyl)propionate Organic Ultraviolet Absorber (e)
    HOB: 2-(2-Hydroxy-5-tert-octylphenyl)benzotriazole Stabilizers Other than Hindered Phenolic Compound (d)
    MEHQ: p-Methoxyphenol Examples 1 to 9 and Comparative Examples 1 to 6

The components were mixed at ordinary temperature (20° C.±15° C., JIS (Japanese Industrial Standards) Z 8703:1983) in the proportions shown in Tables 1 and 2 to prepare inks as resin compositions for stereolithography according to Examples 1 to 9 and Comparative Examples 1 to 6.

Shapability

1. Shaping Capability

The ink of each Example and Comparative Example was made into a cubic three-dimensional shaped article measuring 10.000 mm each side, using a stereolithography device (DIGITALWAX® 020D, manufactured by DWS). Shaping capability was determined by visually checking the article with regard to various criteria while shaping the article, including detachment from the pedestal of the stereolithography device, shape discontinuity, and breakage in the container (damage to the coating of the tray filled with the resin composition).

2. Consistency

A 0.05 mm-thick PET film having a square base measuring 50 mm each side was placed on a flat surface, and 0.5 ml of the ink of each Example and Comparative Example was dropped on the center of the film. The film was then allowed to stand for 10 minutes in a 25° C. thermostatic chamber. The ink, spread in circular form on the film, was measured for maximum diameter (longest diameter) and minimum diameter (shortest diameter), and the average was taken to find the ink diameter. Here, the ink diameter was calculated for 3 samples of the ink of each Example and Comparative Example. The mean value of the three measurements was determined as the consistency value. Larger consistency values mean that the ink is more fluid, and has superior shapability. In the test, inks with a consistency value of 30 mm or more have higher fluidity and superior shapability. Inks with a consistency value of 40 mm or more are more favorable.

Shape Precision

The ink of each Example and Comparative Example was made into a cubic three-dimensional shaped article measuring 10.000 mm each side, using a stereolithography device (DIGITALWAX® 020D, manufactured by DWS). After washing the three-dimensional shaped article with ethanol and removing unpolymerized portions of the polymerizable monomer, the dimensions (unit: mm) were measured with a micrometer, and a shape inaccuracy was calculated as a measure of shape precision, using the formula below (n=5). Tables 1 and 2 show the mean values of calculated values. A shape inaccuracy of 1.0% or less means superior shape precision, and generally provides superior conformity when the shaped article is formed into crowns or bridges. The preferred shape inaccuracy is 0.80% or less.

$$\text{Shape inaccuracy (\%)} = \frac{|(\text{measured dimensions}) - 10.0|}{10.0} \times 100$$

Flexural Strength and Flexural Modulus

The composition of each Example and Comparative Example shown in Tables 1 and 2 was formed into a cuboidal shaped article measuring 25.0 mm in length, 2.0 mm in width, and 2.0 mm in thickness, using a stereolithography device (DIGITALWAX® 028J-Plus, manufactured by DWS). After washing the shaped article with ethanol and removing unpolymerized portions of the polymerizable monomer, the composition was further polymerized for 90 seconds with a dental laboratory LED polymerizer (a Light V, manufactured by J. MORITA TOKYO MFG. Corp. under this trade name) to obtain a cured product. After being polished with silicon carbide paper #300, the cured product was kept in 37° C. water for 24 hours, and measured for flexural strength (three-point flexural strength) and flexural modulus with a precision universal testing machine (Autograph AG-I, 100 kN, manufactured by Shimadzu Corporation under this trade name) at a span length of 20 mm and a crosshead speed of 1 mm/min (n=5). Tables 1 and 2 show the mean values of measured values. The mechanical strength is superior when the cured product has a flexural strength of 100 MPa or more, and a flexural modulus of 5.0 GPa or more.

Sedimentation

The resin composition for stereolithography (ink, 1 ml) was filled into a 2 ml polypropylene tube vial for centrifugation, and the presence or absence of separation was determined by visually inspecting the composition after centrifugation performed at 5,000 rpm for 5 minutes with a centrifuge (MCX-150, manufactured by Tomy Seiko Co., Ltd.) (n=1). The results are presented as "Good", meaning no observable separation, and "Poor", meaning that separation was observed.

Shade and Shade Stability

The ink of each Example and Comparative Example was made into a disc-shaped shaped article measuring 15.0 mm in diameter and 1.0 mm in thickness, using the same stereolithography device used above. After washing the shaped article with ethanol and removing unpolymerized portions of the polymerizable monomer, the composition was allowed to undergo 5 minutes of secondary polymerization with a dental laboratory LED polymerizer (α Light V, manufactured by J. MORITA TOKYO MFG. Corp. under this trade name) to obtain a cured product. After being polished first with silicon carbide paper #1000, and then with a dental lapping film (manufactured by 3M), the cured product was measured for b* value representing yellowness, and Δb* value representing the extent of yellowing, using a spectrophotometer (SPECTROPHOTOMETER CM-3610A manufactured by Konica Minolta Inc.; in compliance with condition c of JIS Z 8722:2009; D65 illuminant), and mean values were calculated (n=5). Tables 1 and 2 show the mean values. The Δb* value, which represents the extent of yellowing, is defined by the following formula.

$$\Delta b^* = b^*_{(7d)} - b^*_{(0d)},$$

where $b^*_{(7d)}$ represents the mean value of b* value, or yellowness, of the JIS Z 8781-4:2013 L*a*b* color system measured after 7 days from shaping and secondary polymerization, and $b^*_{(0d)}$ represents the mean value of b* value, or yellowness, of the L*a*b*color system measured immediately after shaping and secondary polymerization.

When the b* value or yellowness is 10.0 or less, a dental prosthesis fabricated from the composition is more likely to be perceived as being colorless in visual inspection. The preferred b* value is 8.0 or less. When the Δb* value or extent of yellowing is 5.0 or less, a dental prosthesis fabricated from the composition is more likely to be perceived as having no yellowing in visual inspection. The preferred Δb* value is 4.5 or less.

TABLE 1

| | | Examples | | | | | | | | |
|---|---|---|---|---|---|---|---|---|---|---|
| | | 1 | 2 | 3 | 4 | 5 | 6 | 7 | 8 | 9 |
| Raw materials (parts by mass) | UDMA (a)-1 | 40 | 40 | 40 | 40 | 40 | 40 | 40 | 40 | 40 |
| | Bis-GMA (a)-2 | 20 | 20 | 20 | 20 | 20 | 20 | 20 | 20 | 20 |
| | TEGDMA (a)-3 | 20 | 20 | 20 | 20 | 20 | 20 | 20 | 20 | 20 |
| | ACMO (a)-4 | 20 | 20 | 20 | 20 | 20 | 20 | 20 | 20 | 20 |
| | TPO (b)-1 | 3 | 3 | 3 | 3 | 3 | 3 | 1.5 | 5 | 3 |
| | Inorganic particle (c)-1 | | | | | 150 | | | | |
| | Inorganic particle (c)-2 | 75 | 150 | 200 | 300 | | | 150 | 150 | 150 |
| | Inorganic particle (c)-3 | | | | | | 150 | | | |
| | BHT (d)-1 | 1 | 1 | 1 | 1 | 1 | 1 | 1.5 | 0.25 | |
| | PETBHPP (d)-2 | | | | | | | | | 1 |
| | HOB (e)-1 | 0.5 | 0.5 | 0.5 | 0.5 | 0.5 | 0.5 | 0.5 | 0.5 | 0.5 |
| Properties | Shaping capability | Capable | Capable | Capable | Capable | Capable | Capable | Capable | Capable | Capable |
| | Consistency (mm) | 54 | 48 | 42 | 38 | 43 | 52 | 48 | 49 | 46 |
| | Shape inaccuracy (%) | 0.42 | 0.50 | 0.58 | 0.63 | 0.44 | 0.72 | 0.82 | 0.58 | 0.64 |
| | Flexural strength (MPa) | 115 | 136 | 152 | 158 | 124 | 138 | 118 | 131 | 133 |
| | Flexural modulus (GPa) | 5.4 | 5.8 | 6.2 | 6.4 | 5.3 | 6.1 | 5.2 | 5.5 | 5.6 |
| | Sedimentation | Good | Good | Good | Good | Good | Good | Good | Good | Good |
| | Yellowness (b* value) | 6.1 | 4.8 | 4.2 | 3.9 | 6.3 | 5 | 5.4 | 7.8 | 5.8 |
| | Extent of yellowing (Δb* value) | 4.2 | 3.2 | 2.8 | 2.4 | 4.8 | 2.9 | 3.5 | 4.2 | 3.5 |

TABLE 2

| | | Comparative Examples | | | | | |
|---|---|---|---|---|---|---|---|
| | | 1 | 2 | 3 | 4 | 5 | 6 |
| Raw materials (parts by mass) | UDMA (a)-1 | 40 | 40 | 40 | 40 | 40 | 40 |
| | Bis-GMA (a)-2 | 20 | 20 | 20 | 20 | 20 | 20 |
| | TEGDMA (a)-3 | 20 | 20 | 20 | 20 | 20 | 20 |
| | ACMO (a)-4 | 20 | 20 | 20 | 20 | 20 | 20 |
| | TPO (b)-1 | 3 | 3 | 3 | 5 | 0.2 | 3 |
| | Inorganic particle (c)-1 | | | | | | |
| | Inorganic particle (c)-2 | 25 | 500 | | 150 | 150 | 150 |
| | Inorganic particle (c)-3 | | | | | | |
| | Inorganic particle (large particle size) | | | 150 | | | |
| | BHT (d)-1 | 1 | 1 | 1 | 0.001 | 1.5 | |
| | PETBHPP (d)-2 | | | | | | |
| | HOB (e)-1 | 0.5 | 0.5 | 0.5 | 0.5 | 0.5 | 0.5 |
| | MEHQ | | | | | | |
| Properties | Shaping capability | Capable | Incapable | Capable | Capable | Incapable | Capable |
| | Consistency (mm) | 59 | 28 | 50 | 48 | 48 | 48 |
| | Shape inaccuracy (%) | 0.47 | — | 1.23 | 0.48 | — | 0.52 |
| | Flexural strength (MPa) | 88 | — | 118 | 132 | — | 132 |
| | Flexural modulus (GPa) | 3.2 | — | 5.6 | 5.8 | — | 5.4 |
| | Sedimentation | Good | Good | Poor | Good | Good | Good |
| | Yellowness (b* value) | 4.9 | — | 5.2 | 12.1 | — | 14.2 |
| | Extent of yellowing (Δb* value) | 4.7 | — | 3.8 | 8.6 | — | 10.1 |

As shown in Tables 1 and 2, the resin compositions for stereolithography of Examples 1 to 9 had shapable consistencies, and the shape precision was superior with no sedimentation of inorganic particles occurring during storage. The cured products of the resin compositions for stereolithography of Examples 1 to 9 had superior flexural strength and flexural modulus, and discoloration was small. The composition of Comparative Example 1 containing a smaller amount of inorganic particle (c) had low flexural strength and low flexural modulus. The composition of Comparative Example 2 containing a large amount of inorganic particle (c) was unshapable because of the excessively low consistency. In the composition of Comparative Example 3 containing large inorganic particles, sedimentation of inorganic particles occurred, and the shape precision was inferior. The extent of coloring and discoloration was large in the composition of Comparative Example 4 in which the content of hindered phenolic compound (d) was excessively low with respect to the content of photopolymerization initiator (b). The composition was unshapable in Comparative Example 5 in which the content of hindered phenolic compound (d) was excessively high with respect to the content of photopolymerization initiator (b). The extent of coloring and discoloration was large in the composition of Comparative Example 6 that did not contain a hindered phenolic compound but contained other stabilizer instead.

INDUSTRIAL APPLICABILITY

A resin composition for stereolithography of the present invention is easily shapable with good shape precision while reducing sedimentation of inorganic particles during storage, and a obtained three-dimensional shaped article thereby excels in mechanical characteristics such as flexural strength and flexural modulus, in addition to having a desirable shade and good shade stability. This makes a resin composition for stereolithography of the present invention suitable for dental materials, particularly dental prostheses.

The invention claimed is:

1. A resin composition for stereolithography comprising a polymerizable monomer (a), a photopolymerization initiator (b), an inorganic particle (c) having an average particle diameter of 5 to 500 nm, and a hindered phenolic compound (d), wherein
the content of the photopolymerization initiator (b) is 0.1 to 10 parts by mass relative to 100 parts by mass of the polymerizable monomer (a),
the content of the inorganic particle (c) is 50 to 400 parts by mass relative to 100 parts by mass of the polymerizable monomer (a), and
the content of the hindered phenolic compound (d) is 5.0 to 500 parts by mass relative to 100 parts by mass of the photopolymerization initiator (b).

2. The resin composition for stereolithography according to claim 1, which has a consistency at 25° C. of 30 mm or more.

3. The resin composition for stereolithography according to claim 1, wherein the inorganic particle (c) is surface-treated.

4. The resin composition for stereolithography according to claim 1, wherein the inorganic particle (c) comprises a spherical inorganic particle (c-I).

5. The resin composition for stereolithography according to claim 4, wherein the spherical inorganic particle (c-I) has a sphericity of 0.70 to 0.99.

6. The resin composition for stereolithography according to claim 1, wherein the inorganic particle (c) has an average particle diameter of 7.5 to 300 nm.

7. The resin composition for stereolithography according to claim 1, wherein the inorganic particle (c) has an average particle diameter of 10 to 200 nm.

8. The resin composition for stereolithography according to claim 1, comprising no inorganic particles other than an inorganic particle (c).

9. The resin composition for stereolithography according to claim 1, which further comprises an organic ultraviolet absorber (e).

10. The resin composition for stereolithography according to claim 1, wherein the polymerizable monomer (a) comprises an aromatic bifunctional polymerizable monomer.

11. The resin composition for stereolithography according to claim 10, wherein the aromatic bifunctional polymerizable monomer is at least one selected from the group consisting of 2,2-bis [4-(3-methacryloyloxy-2-hydroxypropoxy)phenyl] propane, and 2,2-bis(4-(meth)acryloyloxy-polyethoxyphenyl) propane.

12. The resin composition for stereolithography according to claim 1, wherein the polymerizable monomer (a) comprises a monofunctional monomer.

13. The resin composition for stereolithography according to claim 12, wherein the monofunctional monomer comprises a (meth)acrylamide polymerizable monomer.

14. The resin composition for stereolithography according to claim 1, wherein the hindered phenolic compound (d) comprises a compound represented by the following general formula [I], and/or a compound represented by the following general formula [III]:

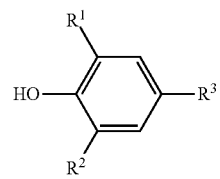

wherein $R^1$ to $R^3$ each independently represent an optionally substituted alkyl group having 1 to 20 carbon atoms, an optionally substituted alkoxy group having 1 to 20 carbon atoms, an optionally substituted aryl group having 6 to 12 carbon atoms, or a hydroxyl group, and the groups represented by $R^1$ to $R^3$ (excluding the hydroxyl group) may contain at least one binding group selected from the group consisting of —O—, —S—, —NH—, —N($R^4$)—, —O(CO)—, and —CO—, where $R^4$ represents an alkyl group having 1 to 6 carbon atoms,

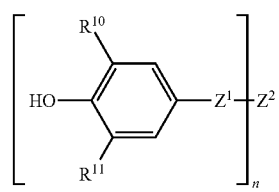

wherein $R^{10}$ and $R^{11}$ each independently represent an optionally substituted alkyl group having 1 to 20 carbon atoms, an optionally substituted alkoxy group having 1 to 20 carbon atoms, or an optionally substituted aryl group having 6 to 12 carbon atoms, $Z^1$ represents an optionally substituted alkylene group having 1 to 20 carbon atoms, $Z^2$ represents a carbon atom, an oxygen atom, a nitrogen atom, a sulfur atom, or an aryl group, n represents an integer of 2 to 6, and the groups represented by $R^{10}$, $R^{11}$, and $Z^1$ may contain at least one binding group selected from the group consisting of —O—, —S—, —NH—, —N($R^{12}$)—, —O(CO)—, and —CO—, where $R^{12}$ represents an alkyl group having 1 to 6 carbon atoms.

15. The resin composition for stereolithography according to claim 14, wherein the hindered phenolic compound (d) comprises a compound represented by general formula [III].

16. The resin composition for stereolithography according to claim 15, wherein the alkylene group represented by Z' in a compound represented by the general formula [III] is interrupted by at least one binding group selected from the group consisting of —O—, —S—, —NH—, —N($R^{12}$)—, —O(CO)—, and —CO—.

17. The resin composition for stereolithography according to claim 1, wherein the content of the hindered phenolic compound (d) is 5.0 to 100 parts by mass relative to 100 parts by mass of the photopolymerization initiator (b).

18. A dental material comprising a cured product of a resin composition for stereolithography of claim 1.

19. A dental prosthesis comprising a cured product of a resin composition for stereolithography of claim 1.

20. A method for producing a three-dimensional shaped article by photo-solidification with a resin composition for stereolithography of claim 1.

21. The method according to claim 20, wherein the photo-solidification is bottom-up vat stereolithography.

22. A resin composition for stereolithography comprising a polymerizable monomer (a), a photopolymerization initiator (b), an inorganic particle (c) having an average particle diameter of 5 to 500 nm, and a hindered phenolic compound (d), wherein
the content of the photopolymerization initiator (b) is 0.1 to 10 parts by mass relative to 100 parts by mass of the polymerizable monomer (a),
the content of the inorganic particle (c) is 50 to 400 parts by mass relative to 100 parts by mass of the polymerizable monomer (a), and
the content of the hindered phenolic compound (d) is 0.1 to 500 parts by mass relative to 100 parts by mass of the photopolymerization initiator (b),
and wherein the hindered phenolic compound (d) comprises a compound represented by the following general formula [III]:

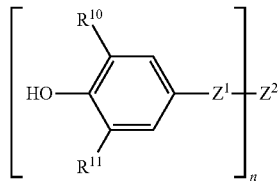

wherein $R^{10}$ and $R^{11}$ each independently represent an optionally substituted alkyl group having 1 to 20 carbon atoms, an optionally substituted alkoxy group having 1 to 20 carbon atoms, or an optionally substituted aryl group having 6 to 12 carbon atoms, $Z^1$ represents an optionally substituted alkylene group having 1 to 20 carbon atoms, $Z^2$ represents a carbon atom, an oxygen atom, a nitrogen atom, a sulfur atom, or an aryl group, n represents an integer of 2 to 6, and the groups represented by $R^{10}$, $R^{11}$, and $Z^1$ may contain at least one binding group selected from the group consisting of —O—, —S—, —NH—, —N($R^{12}$)—, —O(CO)—, and —CO—, where $R^{12}$ represents an alkyl group having 1 to 6 carbon atoms.

23. The resin composition for stereolithography according to claim 22, wherein the alkylene group represented by 21 in a compound represented by the general formula [III] is interrupted by at least one binding group selected from the group consisting of —O—, —S—, —NH—, —N($R^{12}$)—, —O(CO)—, and —CO—.

* * * * *